United States Patent [19]

Chastain et al.

[11] Patent Number: 5,755,766
[45] Date of Patent: May 26, 1998

[54] OPEN-ENDED INTRAVENOUS CARDIAC LEAD

[75] Inventors: Stuart R. Chastain, Shoreview; Bruce A. Tockman, Scandia; Randy W. Westlund, Minneapolis, all of Minn.

[73] Assignee: Cardiac Pacemakers, Inc., St. Paul, Minn.

[21] Appl. No.: 787,308

[22] Filed: Jan. 24, 1997

[51] Int. Cl.⁶ .................................................. A61N 1/05
[52] U.S. Cl. .......................... 607/122; 607/120; 607/119
[58] Field of Search .............................. 607/119, 122, 607/125, 120

[56] References Cited

U.S. PATENT DOCUMENTS

| | | |
|---|---|---|
| 4,932,407 | 6/1990 | Williams . |
| 5,014,696 | 5/1991 | Mehra . |
| 5,016,646 | 5/1991 | Gotthardt et al. ............ 607/122 |
| 5,099,838 | 3/1992 | Bardy . |
| 5,324,324 | 6/1994 | Vachon et al. . |
| 5,348,021 | 9/1994 | Adams et al. . |
| 5,350,404 | 9/1994 | Adams et al. . |
| 5,433,729 | 7/1995 | Adams et al. . |
| 5,458,621 | 10/1995 | White et al. . |
| 5,476,498 | 12/1995 | Ayers ........................... 607/122 |
| 5,545,204 | 8/1996 | Cammilli et al. . |
| 5,609,622 | 3/1997 | Soukup et al. ................ 607/122 |

FOREIGN PATENT DOCUMENTS 388480  9/1990  WIPO .

*Primary Examiner*—William E. Kamm
*Assistant Examiner*—Carl H. Layno
*Attorney, Agent, or Firm*—Haugen and Nikolai, P.A.

[57] ABSTRACT

Intravenous cardiac leads having at least one electrode intended to be implanted within the coronary veins are disclosed. Also disclosed are structures and techniques for advancing such leads through the atrium and coronary sinus into the coronary veins overlaying the left ventricle.

26 Claims, 4 Drawing Sheets

OPEN-ENDED INTRAVENOUS CARDIAC LEAD

BACKGROUND OF THE INVENTION

I. Field of the Invention

This invention relates to cardiac leads used in combination with a cardiac rhythm management device, e.g., heart pacemakers or defibrillator, to monitor and control the rhythm of the heart. This invention is more particularly directed toward lead configurations adapted to be implanted in the coronary veins on the left side of the heart and to methods for implanting such leads.

II. Discussion of the Prior Art

As explained in U.S. Pat. No. 4,928,688 to Morton M. Mower dated May 29, 1990, under normal circumstances impulses from the SA node affect contraction of the atria and then propagate to the AV node. The AV node then emits a second nerve impulse which affects contraction of the ventricles. In healthy individuals this is done in a coordinated manner to circulate blood through the body. However, many patients suffer from conditions which inhibit the transfer of nerve impulses from the SA node to the AV node and from there to the ventricles. In such cases, the chambers of the heart do not contract in a coordinated fashion and hemodynamic efficiency of the heart is decreased. This has profound adverse implications for the health and well-being of the patient. In minor cases, the quality of life is considerably reduced. More severe cases can result in death.

The Mower U.S. Pat. No. 4,928,688 describes a method for improving the hemodynamic efficiency of a sick heart. The method proposed in that patent is to place electrodes in both the right and left ventricles, monitor the cardiac signals originating in the right and left ventricles, analyze these signals and the absence thereof in a control circuit, and provide stimulating pulses to one or both ventricles within a time interval designed to improve the heart's hemodynamic efficiency.

Others have discussed the advantages of implanting leads in both the right and left ventricles to permit a sick heart to be more effectively defibrillated. See, for example, U.S. Pat. No. 4,922,407 to Williams; U.S. Pat. No. 5,099,838 to Bardy; and U.S. Pat. Nos. 5,348,021, 5,433,729, and 5,350,404 all to Adams et al. Each of the patents describe inserting a lead through the right atrium and coronary sinus into one of the coronary veins. None of these patents, however, discuss the difficulties encountered in doing so.

Important health advantages are achieved by positioning an electrode in a branch of the great vein of the heart. A lead so positioned can be used to stimulate the left ventricle. While it would be possible to position the electrode within the left ventricle, this can increase the potential for clot formation. If such a clot were released to the brain, the situation could be life threatening. However, traditional leads are not well suited for implantation in the coronary vein. Traditional leads tend to be too big, tend to have some type of fixation device (such as tines or a screw) that must be altered to advance the lead into the sinus, or tend to require a style for positioning which is not flexible enough to negotiate the coronary vessels.

An arrangement intended to address such difficulties associated with the implantation of leads is disclosed in U.S. Pat. No. 5,304,218 granted to Clifton A. Alertness on Apr. 19, 1994. The arrangement disclosed in this patent includes a lead having an electrode. The electrode has a follower means for slid ably engaging a guide wire. The electrode is implanted by feeding the guide wire along the desired path, engaging the follower means to the guide wire, advancing the lead along the guide wire until the electrode resides at the implant site, and retracting the guide wire from the follower means after the electrode is implanted at the implant site.

A review of the specification and drawings of U.S. Pat. No. 5,304,218 and an understanding of the anatomy and physiology of the heart demonstrates several problems with this approach. First, the path through which the lead must be fed is very restricted. The increased size of the distal end of the lead, given the presence of the follower, may make it more difficult to advance such a lead along the desired path so as to be positioned on myocardial tissue of the left ventricle. Second, the direction of blood flow through the veins tends to force electrodes implanted there out of the vein. This problem is likely to be exacerbated by the increase in the profile area of the distal end given the presence of the follower. Third, the profile of the distal end of a lead implanted in a coronary vein may need to be made as small as possible to limit occlusion and permit blood to flow as freely as possible through the blood vessel when the lead is in place and to limit damage to the vessels and/or myocardium.

SUMMARY OF THE INVENTION

The present invention provides an improved lead for implantation of an electrode into a coronary vein on the left side of the heart. The lead includes an elongated, flexible body member made of an electrically insulative material. The body member includes a proximal end and a distal end. A lumen extends through the body member from the proximal end toward the distal end. The lumen may extend all the way to the distal end so that the distal end includes an opening. The lead also includes a conductive member extending through the body member from the proximal end toward the distal end. Electrically coupled to the conductive member near its distal end is an electrode. Additional lumens, electrodes and conductive members may be included within and on the lead body.

Leads made in conformance with the present invention can be inserted in a number of different ways. For example, a guide catheter can be inserted and then the lead passed through the guide catheter until it is properly positioned. The lead can be coated with a lubricious coating to reduce friction in the guide catheter. The guide catheter can then be retracted. Similarly, a guide wire can be advanced to the implant site alone or through a guide catheter. Using the open distal lumen, the lead can be slid over the guide wire until the electrode is properly positioned. The guide wire or guide catheters can then be retracted. Also, the lead can be temporarily fixed to a guide catheter. The fixate may be designed to be dissolved by body fluids. The lead is then inserted along with the guide catheter. After the electrode is in place and the fixate dissolves, the guide catheter can be retracted.

Alternative embodiments of the present invention offer other advantages and features. For example, the wall of the lumen can be coated with a lubricious coating or a polymer with a low coefficient of friction to reduce friction between a guide wire and the wall of the lumen. The lumen can also be used to deploy a separate electrode past the distal end of the lead's body member. Additional lumens can be provided and the cross-section of the body member can be modified to provide a channel for a guide wire. These features are shown in the drawings and discussed in further detail below.

DETAILED DESCRIPTION OF THE INVENTION

Figure 1:
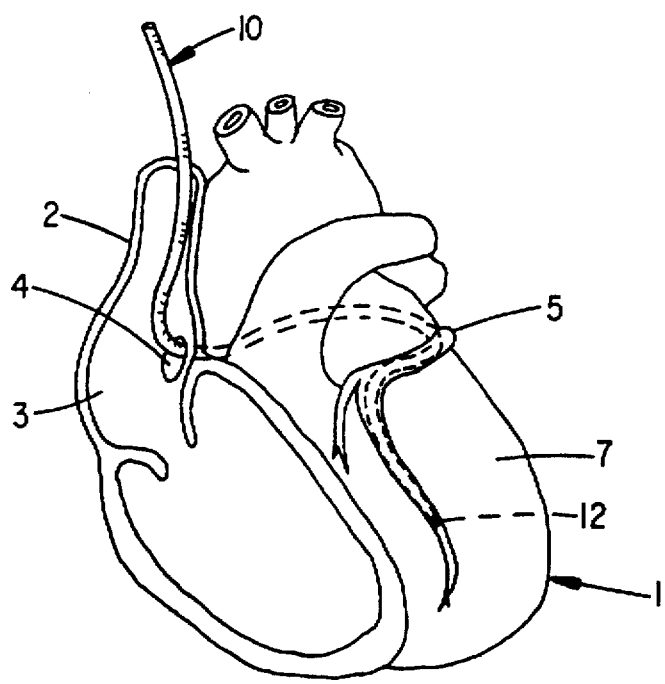
FIG. 1 is a plan view of an intravenous cardiac lead having an electrode positioned in a coronary vein.

FIG. 1 shows a human heart 1 with the intravenous coronary lead 10 of the present invention passing through the superior vena cava 2, the right atrium 3, and the coronary sinus 4 into the great vein of the heart 5 so that a surface electrode 12 on the lead 10 is implanted in a branch of the coronary vein. When positioned as shown, the electrode 12 can be used to sense the electrical activity of the heart or to apply a stimulating pulse to the left ventricle 7 and without the need of being in the left ventricular chamber.

Figure 2:
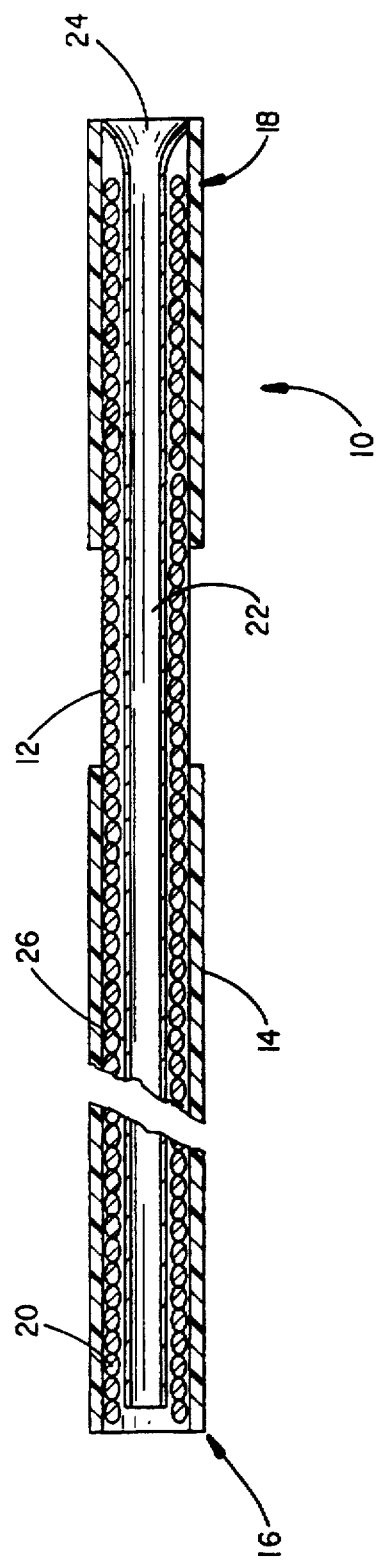
FIG. 2 is a cross-section of a distal end portion of the intravenous cardiac lead shown in FIG. 1.

FIG. 2 shows in greater detail the structure of the intravenous coronary lead shown in FIG. 1. As shown in FIG. 2, the lead 10 includes an elongated body member 14 having a proximal end 16 and a distal end 18. The body member 14 is preferably made of a flexible, electrically insulative material. The outer surface of the body member 14 is preferably treated to prevent fibrotic attachment and to reduce inflammation response to the lead. Such a treatment could include a carbon coating, a steroid embedded in the material, a steroid eluting collar, or the like.

The body member 14 encapsulates a flexible electrically conductive member 20 extending from the proximal end 16 toward the distal end 18 of the lead's body member 14. Conductive member 20 is shown as a flexible wire coil in FIG. 2. Alternatively, the conductor member 20 could be in the form of a conductive wire, a thin ribbon, a plurality of fine wires formed as a cable, or a flexible tube without deviating from the invention.

FIG. 2 also shows the lead 10 as including a central lumen 22 extending from the proximal end 16 to the distal end 18 of the body member 14. In fact, in this embodiment, there is an opening 24 through the distal end 18 to the lumen 22. A coating of a material such as polytetrafluoroethylene (Teflon) preferably forms the wall 26 of the lumen 22 to increase its lubricity. The coating material, of course, could be some other polymer having a low coefficient of friction.

The electrode 12 shown in FIG. 2 is preferably created by removing an annular portion of the insulative body member 14 to expose a portion of the underlying conductive member 20. When the conductive member 20 is a coil as shown in FIG. 2, the turns of the coil can be melt-banded such as by application of laser energy, to form the surface electrode 12. Those skilled in the art will recognize that a ring electrode electrically coupled to the conductive member 20 will also suffice. Likewise, the position of the electrode 12 along the body member 14 can be changed. Certain advantages may be achieved, for example, if the electrode 12 is at the tip of the lead.

The lumen 22 can be put to many uses. For example, a surgeon can advance a guide wire through the coronary sinus and coronary veins to the proper position for the electrode 12. The free proximal end of the guide wire can then be inserted through the opening 24 in the distal end 18 and the lead 10 slid over the guide wire to position the electrode 12. The guide wire can then be retracted through the lumen 22. The lumen 22 can also be used to insert a small separate structure with an electrode or sensor deployable beyond the tip of the lead. This allows separation of the electrodes and can be used for bipolar pacing or for a combination of pacing and defibrillation. Likewise, the lumen could be used to inject a contrast fluid to facilitate fluoroscopic viewing. The lumen can also be used to deploy a fixation mechanism, deploy an extraction mechanism, or deploy a plug to close the opening 24 and seal the lumen.

Figure 3:
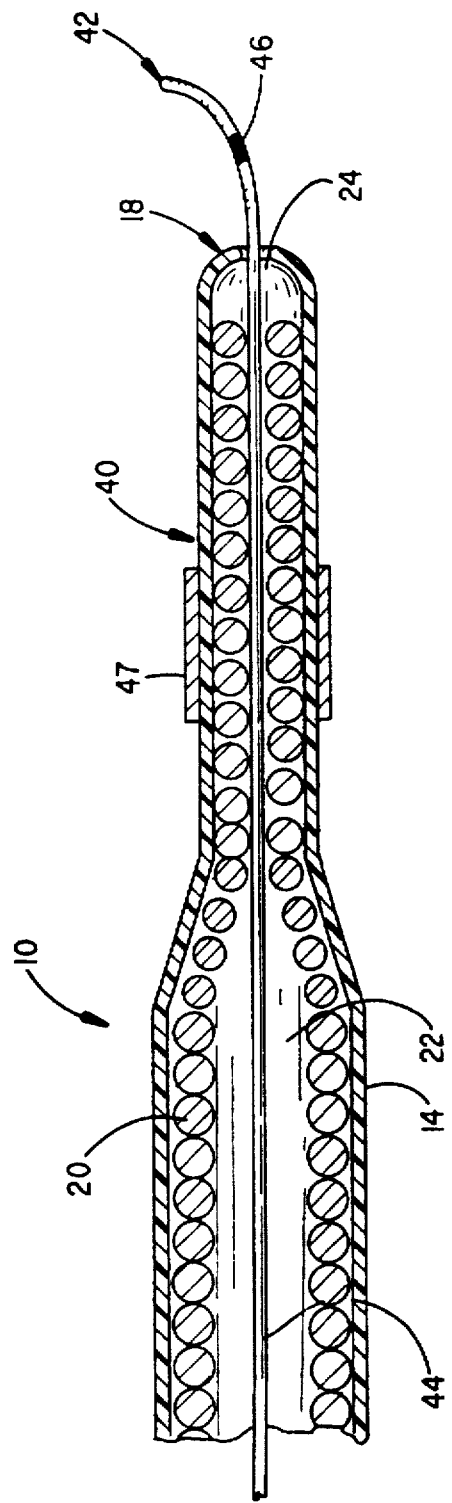
FIG. 3 is a longitudinal cross-section view of a distal end portion of an intravenous coronary lead of the present invention with a tapered end and deployable electrode.

FIG. 3 shows how the lead 10 can be modified to provide a tip 40 of a reduced diameter. The body member 14 of lead 10 has a distal end 18 with an opening 24 in communication with the lumen 22. FIG. 3 shows how the lumen 22 can be used to deploy a separate structure such as second, miniaturized lead 42. The deployable lead 42 has a lead body 44, an electrode 46 and a conductive member (not shown) coupled to electrode 46 and running from the electrode 46 to the proximal end of the lead body 44. The lead body 44 may be designed to coil after it exits the lumen to fix the electrode 46 in the correct position. FIG. 3 also shows a ring electrode 47 surrounding a portion of the tip 40. The ring electrode 47, when present, is electrically coupled to conductive member 20. Additional electrodes and conductors can be added for sensing, pacing or defibrillating as desired. As indicated above, the ring electrode can also be formed by exposing and laser bonding the coils of the conductive member 20. The electrode 46 may be multipolar. It can be used for defibrillating and the electrode 47 is used for pacing. Alternatively, electrode 46 may be used for pacing and the electrode 47 used for pacing. Electrodes 47 and 46 could also be used for sensing electrical activity of the heart. Electrodes 47 and 46 can also be used together for bipolar pacing. Without limitation, the main portion of body member 14 could have an outside diameter in the range of 0.020 inches to 0.100 inches. If, for example, the main portion of the body member has an outside diameter of 0.058 inches, the diameter of the tip 40 could have an outside diameter of approximately 0.046 inches and the deployable lead 42 could have an outside diameter of 0.014 inches. When used, the main lead body can be positioned first over a guide wire. Once the lead is in place the guide wire is removed and replaced with the deployable structure which can be advanced beyond the tip of the larger lead body.

Figure 4:
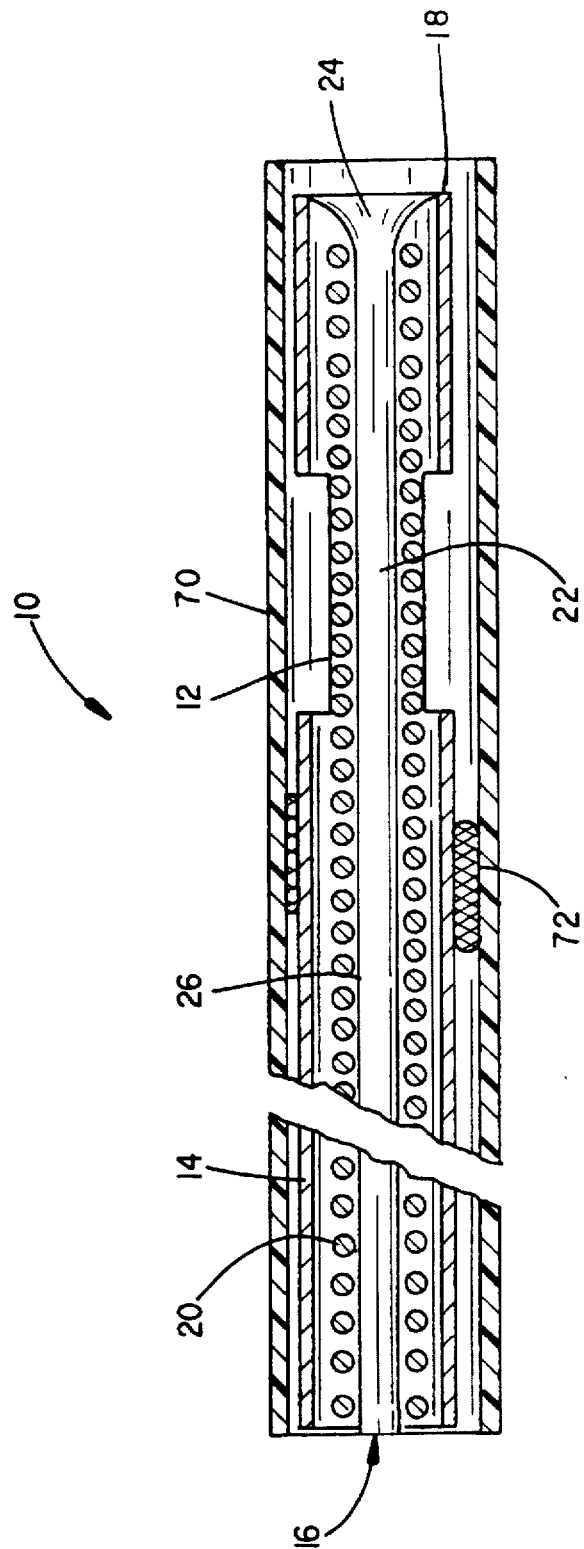
FIG. 4 is a longitudinal cross-section of a distal end portion of an intravenous coronary lead inserted within and temporarily fixed to a guide catheter.

FIG. 4 is provided to assist in explaining an alternative method for implanting an electrode 12 in a coronary vein. As shown in FIG. 4, the lead 10 is loaded and temporarily fixed to the inside of a guide catheter 70 designed to be placed in the coronary sinus. The fixation means 72 may consist of a material such as mannitol which will dissolve after short exposure to blood. Once the guide catheter 70 is properly positioned and the fixation means 72 is dissolved, the guide catheter 70 can be retracted leaving the lead in place with an electrode at a desired position. The lead can then be advanced further if necessary using a stylet and/or guide wire as previously described.

While not shown in any of the views, each lead will have one or more connectors of a type known in the art at its proximal end for mating with the pacer and/or defibrillator pulse generator whereby depolarization signals originating in the heart can be sensed and stimulating pulses applied in accordance with the device's control algorithms.

The foregoing discussion is intended to illustrate various preferred arrangements for meeting the objections of the present invention. Modifications and variation can be made by those skilled in the art without departing from the invention. Accordingly, the invention is limited only by the scope of the following claims which are intended to cover all alternate embodiments and modifications as may fall within the true scope of this invention.

What is claimed:

1. For use with a cardiac rhythm management device, an intravenous lead having:
   (a) an elongated, flexible body member made of an electrically insulative material, said body member having a proximal end and a distal end, said body member being of a size to permit the distal end to be advanced through the right atrium and coronary sinus into the coronary veins;
   (b) a lumen extending through the body member from the proximal end toward the distal end of the body member, said lumen having a first opening through the proximal end and a second opening through the distal end of the body member;
   (c) a conductive member extending through the body member from the proximal end toward the distal end of the body member;
   (d) an electrode electrically coupled to said conductive member; and
   (e) a separate structure deployable through the lumen past said second opening, said separate structure including an electrode.

2. The lead of claim 1 wherein the electrode on said separate structure comprises multipolar electrode.

3. The lead of claim 1 wherein the electrode on said separate structure used for pacing and an electrode on the lead body is used for defibrillation.

4. The lead of claim 1 wherein the electrode on said separate structure is used for defibrillation and an electrode on the lead body is used for pacing.

5. The lead of claim 1 wherein the electrode on the separate structure is used along with an electrode on the lead body for bipolar pacing.

6. The lead of claim 1 wherein the distal end of separate structure curls when deployed past the distal end of the elongated, flexible body member to fix an electrode in the desired position.

7. For use with a cardiac rhythm management device, an intravenous lead having:
   (a) an elongated, flexible body member made of an electrically insulative material and having a coating of an anti-inflammatory agent, said body member having a proximal end and a distal end, said body member being of a size to permit the distal end to be advanced through the right atrium and coronary sinus into the coronary veins;
   (b) a lumen extending through the body member from the proximal end toward the distal end of the body member, said lumen having a first opening through the proximal end and a second opening through the distal end of the body member;
   (c) a conductive member extending through the body member from the proximal end toward the distal end of the body member; and
   (d) an electrode electrically coupled to said conductive member.

8. For use with a cardiac rhythm management device, an intravenous lead having:
   (a) an elongated, flexible body member made of an electrically insulative material, said body member having a proximal end and a distal end, said body member being of a size to permit the distal end to be advanced through the right atrium and coronary sinus into the coronary veins;
   (b) a lumen extending through the body member from the proximal end toward the distal end of the body member, said lumen having a first opening through the proximal end and a second opening through the distal end of the body member;
   (c) a conductive member extending through the body member from the proximal end toward the distal end of the body member;
   (d) an electrode electrically coupled to said conductive member; and
   (e) dissolvable means for securing the lead to a guide member.

9. For use with a cardiac rhythm management device, an intravenous lead having:
   (a) an elongated, flexible body member made of an electrically insulative material, said body member having a proximal end and a distal end, said body member being of a size to permit the distal end to be advanced through the right atrium and coronary sinus into the coronary veins;
   (b) a lumen extending through the body member from the proximal end toward the distal end of the body member, said lumen having a first opening through the proximal end and a second opening through the distal end of the body member;
   (c) a conductive member extending through the body member from the proximal end toward the distal end of the body member;
   (d) an electrode electrically coupled to said conductive member; and
   (e) an extraction mechanism deployable through the lumen past said second opening through the distal end of the body member.

10. For use with a cardiac rhythm management device, an intravenous lead having:
   (a) an elongated, flexible body member made of an electrically insulative material, said body member having a proximal end and a distal end, said body member being of a size to permit the distal end to be advanced through the right atrium and coronary sinus into the coronary veins;
   (b) a lumen extending through the body member from the proximal end toward the distal end of the body member, said lumen having a first opening through the proximal end and a second opening through the distal end of the body member so that a contrasting fluid can be injected through said lumen and out of the distal end of the body member through said second opening;
   (c) a conductive member extending through the body member from the proximal end toward; and
   (d) an electrode electrically coupled to said conductive member.

11. The lead defined by claims 1, 7, 8, 9 or 10 wherein said lead has a sleeve made of a polymer with a low coefficient of friction lining the wall of said lumen.

12. The lead defined by claims 1, 7, 8, 9 or 10 wherein said conductive member comprises a helical coil.

13. The lead defined by claims 1, 7, 8, 9 or 10 wherein said conductive member comprises a tube made of a conductive polymer.

14. The lead defined by claims 1, 7, 8, 9 or 10 wherein said electrode comprises an opening in the body member exposing a portion of the conductive member.

15. The lead defined by claims 1, 7, 8, 9 or 10 wherein said electrode is a ring electrode affixed to the surface of the body member and electrically coupled to said conductive member.

16. The lead defined by claims 1, 7, 8, 9 or 10 further including a second electrode.

17. The lead defined by claims 1, 7, 8, 9 or 10 including a plurality of electrodes.

18. The lead of claims 1, 7, 8, 9 or 10 having a separate structure deployable past the distal end through the lumen, said separate structure including an electrode.

19. The lead of claims 1, 7, 8, 9 or 10 wherein the distal end of the elongated, flexible body member has a tapered shape.

20. The lead of claims 1, 7, 8, 9 or 10 wherein said body member further comprises a coating of an anti-inflammatory agent.

21. The lead of claims 1, 8, 9, or 10 wherein said lead body member further comprises a coating of an antifibrotic agent.

22. The lead of claims 1, 7, 9, or 10 further including dissolvable means for securing the lead to a guide catheter.

23. The lead of claims 1, 8, 9, or 10 having a fixation mechanism deployable past the distal end through the lumen.

24. The lead of claims 1, 7, 8 or 10 having an extraction mechanism deployable past the distal end through the lumen.

25. The lead of claims 1, 7, 8, 9 or 10 having a plug to seal the lumen.

26. The lead of claims 1, 7, 8 or 9 wherein a contrast fluid can be injected through said lumen and out the opening in the distal end.

* * * * *

UNITED STATES PATENT AND TRADEMARK OFFICE
CERTIFICATE OF CORRECTION

PATENT NO. : 5,755,766
DATED : May 26, 1998
INVENTOR(S) : Stuart R. Chastain, et al It is certified that error appears in the above-indentified patent and that said Letters Patent is hereby corrected as shown below:

Claim 15, column 6, line 65 delete "is" and insert -- comprises --.

Claim 20, column 7, line 11 delete "7".

Signed and Sealed this

Twenty-eighth Day of July, 1998

*Attest:*

BRUCE LEHMAN

*Attesting Officer*     *Commissioner of Patents and Trademarks*

US005755766C1

(12) EX PARTE REEXAMINATION CERTIFICATE (4911th)
United States Patent
Chastain et al.

(10) Number: US 5,755,766 C1
(45) Certificate Issued: Feb. 24, 2004

(54) OPEN-ENDED INTRAVENOUS CARDIAC LEAD

(75) Inventors: Stuart R. Chastain, Shoreview, MN (US); Bruce A. Tockman, Scandia, MN (US); Randy W. Westlund, Minneapolis, MN (US)

(73) Assignee: Cardiac Pacemakers, Inc., St. Paul, MN (US)

Reexamination Request:
No. 90/006,157, Dec. 14, 2001

Reexamination Certificate for:
Patent No.: 5,755,766
Issued: May 26, 1998
Appl. No.: 08/787,308
Filed: Jan. 24, 1997

Certificate of Correction issued Jul. 28, 1998.

(51) Int. Cl.⁷ .................................................. A61N 1/05
(52) U.S. Cl. ....................... 607/122; 607/120; 607/119; 600/381
(58) Field of Search ................................ 607/119, 120, 607/122, 125; 600/373–381

(56) References Cited

U.S. PATENT DOCUMENTS

| | | |
|---|---|---|
| 3,769,984 A | 11/1973 | Muench ...................... 128/404 |
| 4,011,875 A | 3/1977 | Lehr et al. |
| 4,106,512 A | 8/1978 | Bisping ....................... 128/418 |
| 4,146,036 A | 3/1979 | Dutcher et al. ............. 128/418 |
| 4,185,639 A | 1/1980 | Linder |
| 4,217,913 A | 8/1980 | Dutcher ...................... 128/785 |
| 4,282,885 A | 8/1981 | Bisping |
| 4,311,153 A | 1/1982 | Smits ......................... 128/785 |
| 4,355,646 A | 10/1982 | Kallok et al. |
| 4,667,686 A | 5/1987 | Peers-Travarton .......... 128/785 |
| 4,934,381 A | 6/1990 | MacGregor |
| 5,003,990 A | 4/1991 | Osypka |
| 5,304,218 A | 4/1994 | Alferness |
| 5,313,943 A | 5/1994 | Houser et al. |
| 5,381,790 A | 1/1995 | Kanesaka |
| 5,487,385 A | 1/1996 | Avitall |
| 5,514,173 A | 5/1996 | Rebell et al. |
| 5,520,194 A | 5/1996 | Miyata et al. |
| 5,584,873 A | 12/1996 | Shoberg et al. |
| 5,643,231 A * | 7/1997 | Lurie et al. .................. 606/232 |
| 5,755,765 A | 5/1998 | Hyde et al. |
| 5,782,239 A | 7/1998 | Webster, Jr. |
| 5,782,760 A | 7/1998 | Schaer ........................ 600/381 |
| 5,897,819 A | 4/1999 | Miyata et al. |
| 5,910,364 A | 6/1999 | Miyata et al. |
| 5,957,842 A * | 9/1999 | Littmann et al. ........... 600/381 |
| 6,141,576 A * | 10/2000 | Littmann et al. ........... 600/381 |

FOREIGN PATENT DOCUMENTS

| | | |
|---|---|---|
| EP | 0 057 877 B1 | 8/1982 |
| EP | 0 057 877 A1 | 8/1982 |
| EP | 0 709 111 A2 | 5/1996 |
| EP | 0 709 111 A3 | 11/1997 |
| GB | 2 032 278 A | 5/1990 |

OTHER PUBLICATIONS

Research Disclosure, "Guidewire Placement of Electrical Lead," Oct. 1993, p. 685.
Advances in Pacemaker Technology (M. Schaldach et al. eds., Springer–Verlag, 1975) pp. 30–31.

* cited by examiner

Primary Examiner—Jeffrey R. Jastrzab

(57) ABSTRACT

Intravenous cardiac leads having at least one electrode intended to be implanted within the coronary veins are disclosed. Also disclosed are structures and techniques for advancing such leads through the atrium and coronary sinus into the coronary veins overlaying the left ventricle.

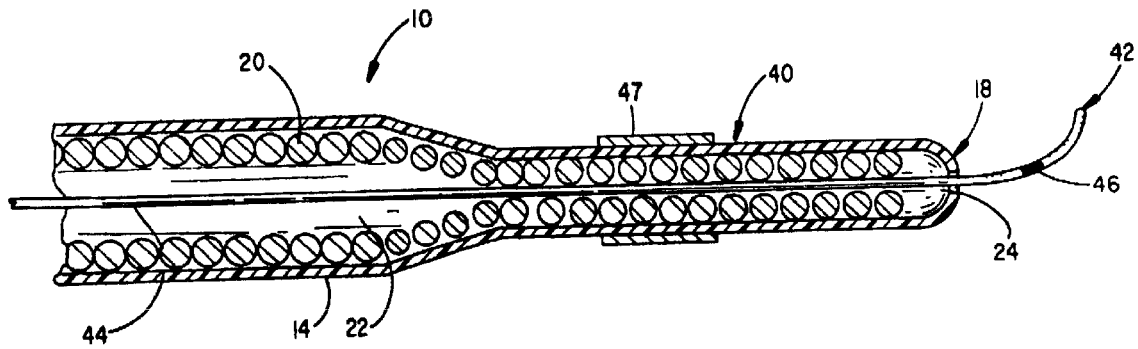

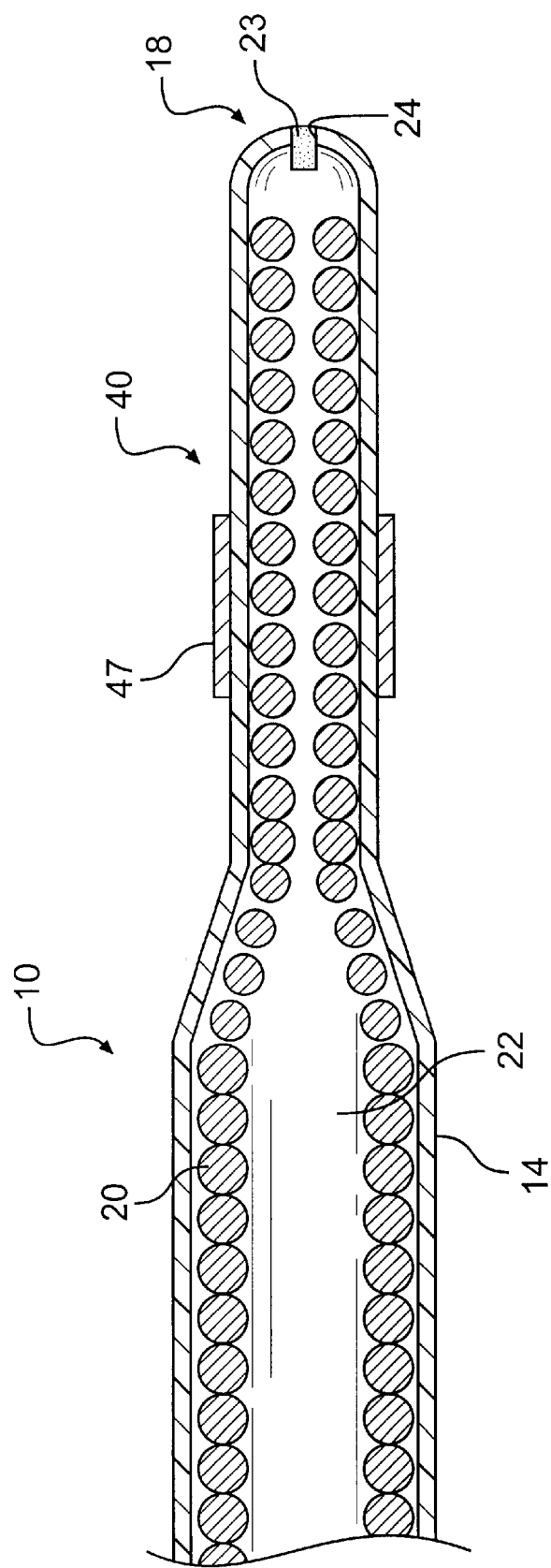
*FIG. 5  NEW*

_EX PARTE_
_REEXAMINATION CERTIFICATE_
_ISSUED UNDER 35 U.S.C. 307_

THE PATENT IS HEREBY AMENDED AS
INDICATED BELOW.

Matter enclosed in heavy brackets [ ] appeared in the
patent, but has been deleted and is no longer a part of the
patent; matter printed in italics indicates additions made
to the patent.

ONLY THOSE PARAGRAPHS OF THE
SPECIFICATION AFFECTED BY AMENDMENT
ARE PRINTED HEREIN.

Column 3, after line 8 add the following paragraph:

*FIG. 5 is a longitudinal cross-section view of a distal end portion of an intravenous coronary lead of the present invention with a plug located in a distal opening of a lumen of the lead.*

Column 3, line 60–Column 4, line 8:

The lumen 22 can be put to many uses. For example, a surgeon an advance a guide wire through the coronary sinus and coronary veins to the proper position for the electrode 12. The free proximal end of the guide wire can then be inserted through the opening 24 in the distal end 18 and the lead 10 slid over the guide wire to position the electrode 12. The guide wire can then be retracted throug the lumen 22. The lumen 22 can also be used to insert a small separate structure with an electrode or sensor deployable beyond the tip of the lead. This allows separation of the electrodes and can be used for bipolar pacing or for a combination of pacing and defibrillation. Likewise, the lumen could be used to inject a contrast fluid to facilitate fluoroscopic viewing. The lumen can also be used to deploy a fixation mechanism, deploy an extraction mechanism, or deploy a plug *23 (FIG. 5)* to close the opening 24 and seal the lumen.

THE DRAWING FIGURES HAVE BEEN
CHANGED AS FOLLOWS:

New figure has been added.

AS A RESULT OF REEXAMINATION, IT HAS BEEN
DETERMINED THAT:

The patentability of claims 7 and 8 is confirmed.

Claims 9, 23, 24 and 26 are cancelled.

Claims 1–6, 10–22 and 25 are determined to be patentable as amended.

New claims 27–235 are added and determined to be patentable.

1. [For] *A* cardiac rhythm management device having an implantable pulse generator for applying pacing pulses to the heart and connected to at least one intravenous lead for use with [a] *the* cardiac rhythm management device, *wherein the improvement comprises* an intravenous lead having:
  (a) an elongated, flexible body member made of an electrically insulative material, said body member having a proximal end and a distal end, said body member being of a size to permit the distal end to be advanced through the right atrium and coronary sinus into the coronary veins;
  (b) a lumen extending through the body member from the proximal end toward the distal end of the body member, said lumen having a first opening through the proximal end and a second opening through the distal end of the body member;
  (c) a conductive member *coupled to the pulse generator and* extending through the body member from the proximal end toward the distal end of the body member;
  (d) an electrode electrically coupled to said conductive member; and
  (e) a separate structure deployable through the lumen past said second opening, said separate structure including an electrode.

2. The [lead] *device* of claim 1 wherein the electrode on said separate structure comprises *a* multipolar electrode.

3. The [lead] *device* of claim 1 wherein the electrode on said separate structure *is* used for pacing and an electrode on the lead body is used for defibrillation.

4. The [lead] *device* of claim 1 wherein the electrode on said separate structure is used for defibrillation and an electrode on the lead body is used for pacing.

5. The [lead] *device* of claim 1 wherein the electrode on the separate structure is used along with an electrode on the lead body for bipolar pacing.

6. The [lead] *device* of claim 1 wherein the distal end of *said* separate structure curls when deployed past the distal end of the elongated, flexible body member to fix an electrode in the desired position.

10. [For] *A* cardiac rhythm management device having an implantable pulse generator for applying pacing pulses to the heart and connected to at least one intravenous lead for use with [a] *the* cardiac rhythm management device, *wherein the improvement comprises* an intravenous lead having:
  (a) an elongated, flexible body member made of an electrically insulative material, said body member having a proximal end and a distal end, said body member being of a size to permit the distal end to be advanced through the right atrium and coronary sinus into the coronary veins;
  (b) a lumen extending through the body member from the proximal end toward the distal end of the body member, said lumen having a first opening through the proximal end and a second opening through the distal end of the body member so that a contrasting fluid can be injected through said lumen and out of the distal end of the body member through said second opening;
  (c) a conductive member *coupled to the pulse generator and* extending through the body member from the proximal end toward *the distal end of the body member, said conductive member comprising a helical coil surrounding said lumen*; and
  (d) an electrode electrically coupled to said conductive member.

11. The [lead] *device* defined by claims 1, 7, 8, [9] or 10 wherein said lead has a sleeve made of a polymer with a low coefficient of friction lining the wall of said lumen.

12. The [lead] *device* defined by claims 1, 7, *or* 8[, 9 or 10] wherein said conductive member comprises a helical coil.

13. The [lead] *device* defined by claims 1, 7, *or* 8[, 9 or 10] wherein said conductive member comprises a tube made of a conductive polymer.

14. The [lead] *device* defined by claims 1, 7, 8, [9] or 10 wherein said electrode comprises an opening in the body member exposing a portion of the conductive member.

15. The [lead] *device* defined by claims 1, 7, 8, [9] or 10 wherein said electrode comprises a ring electrode affixed to the surface of the body member and electrically coupled to said conductive member.

16. The [lead] *device* defined by claims 1, 7, 8, [9] or 10 further including a second electrode *coupled to the body member*.

17. The [lead] *device* defined by claims 1, 7, 8, [9] or 10 including a plurality of electrodes *coupled to the body member*.

18. The [lead] *device* of claims [1,] 7, 8, [9] or 10 having a separate structure deployable past the distal end through the lumen, said separate structure including an electrode.

19. The [lead] *device* of claims 1, 7, 8, [9] or 10 wherein the distal end of the elongated, flexible body member has a tapered shape.

20. The [lead] *device* of claims 1, [,] 8, [9] or 10 wherein said body member further comprises a coating of an anti-inflammatory agent.

21. The [lead] *device* of claims 1, 8, [9] or 10 wherein said lead body member further comprises a coating of an anti-fibrotic agent.

22. The [lead] *device* of claims 1, 7, [9,] or 10 further including dissolvable means for securing the lead to a guide catheter.

25. The [lead] *device* of claims 1, 7, 8, [9] or 10 having a plug to seal the lumen.

27. *The system as claimed in claim 7, wherein said coating comprises a steroid eluting collar.*

28. *The system as claimed in claim 7, wherein the conductive member comprises a helical coil surrounding the lumen.*

29. *The device as claimed in claim 28, wherein said lumen has an inner surface comprising a polymer material with a low coefficient of friction.*

30. *The device as claimed in claim 29, wherein said polymer material is a sleeve contained within the helical coil.*

31. *The device as claimed in claim 7, further comprising a separate structure deployable through the lumen past the second opening.*

32. *The device as claimed in claim 7, wherein said electrode is adapted to be used for defibrillation.*

33. *The device as claimed in claim 7, wherein said electrode is adapted to be used for pacing.*

34. *The device as claimed in claim 33, further comprising a second electrode coupled to the body member.*

35. *The device as claimed in claim 34, wherein said second electrode is adapted to be used for defibrillation.*

36. *The device as claimed in claim 34, wherein said second electrode is adapted to be used for bipolar pacing.*

37. *The device as claimed in claim 7, wherein said electrode is adapted to apply a stimulating pulse to the left ventricle.*

38. *The device as claimed in claim 10, wherein said lumen has an inner surface comprising a polymer material with a low coefficient of friction.*

39. *The device as claimed in claim 38, wherein said polymer material is a sleeve contained within the helical coil.*

40. *The device as claimed in claim 10, further comprising a separate structure deployable through the lumen past the second opening.*

41. *The device as claimed in claim 40, wherein said separate structure includes an electrode.*

42. *The device as claimed in claim 40, wherein said separate structure includes a guide wire.*

43. *The device as claimed in claim 10, wherein said electrode is adapted to be used for defibrillation.*

44. *The device as claimed in claim 10, wherein said electrode is adapted to be used for pacing.*

45. *The device as claimed in claim 44, further comprising a second electrode coupled to the body member.*

46. *The device as claimed in claim 45, wherein said second electrode is adapted to be used for defibrillation.*

47. *The device as claimed in claim 45, wherein said second electrode is adapted to be used for bipolar pacing.*

48. *The device as claimed in claim 45, further including a separate structure deployable through the lumen past the second opening, the separate structure including the second electrode.*

49. *The device as claimed in claim 10, wherein said electrode is adapted to apply a stimulating pulse to the left ventricle.*

50. *The device as claimed in claim 12, wherein said lumen has an inner surface comprising a polymer material with a low coefficient of friction.*

51. *The device as claimed in claim 50, wherein said polymer material is a sleeve contained within the helical coil.*

52. *The device as claimed in claim 20, wherein said coating of an anti-inflammatory agent comprises a carbon coating.*

53. *The device as claimed in claim 20, wherein said coating of an anti-inflammatory agent comprises a steroid.*

54. *The device as claimed in claim 53, wherein said coating comprises a steroid eluting collar.*

55. *For use with a cardiac rhythm management device, an intravenous lead having:*

(a) *an elongated, flexible body member made of an electrically insulative material and having a coating of an anti-inflammatory agent, said coating comprising a steroid, said body member having a proximal end and a distal end, said body member being of a size to permit the distal end to be advanced through the right atrium and coronary sinus into the coronary veins:*

(b) *a lumen extending through the body member from the proximal end toward the distal end of the body member, said lumen having a first opening through the proximal end and a second opening through the distal end of the body member;*

(c) *a conductive member comprising a helical coil formed around said lumen, said conducting member extending through the body member from the proximal end toward the distal end of the body member; and*

(d) *an electrode electrically coupled to said conductive member.*

56. *The lead as claimed in claim 55, wherein said lumen has an inner surface comprising a polymer material with a low coefficient of friction.*

57. *The lead as claimed in claim 56, wherein said polymer material is a sleeve contained within the helical coil.*

58. *The lead as claimed in claim 55, further comprising a separate structure deployable through the lumen past the second opening.*

59. *The lead as claimed in claim 58, wherein said separate structure includes an electrode.*

60. *The lead as claimed in claim 58, wherein said separate structure includes a guide wire.*

61. *The lead as claimed in claim 55, further comprising a plug sealing the lumen.*

62. *The lead as claimed in claim 61, wherein said plug is deployable using said lumen.*

63. The lead as claimed in claim 55, wherein said conductive member comprises a tube of a conductive polymer.

64. The lead as claimed in claim 55, wherein said electrode comprises an opening in the body member exposing a portion of the conductive member.

65. The lead as claimed in claim 55, wherein said electrode is a ring electrode affixed to the surface of the body member and electrically coupled to said conductive member.

66. The lead as claimed in claim 55, wherein said intravenous lead further comprises a second electrode coupled to the body member.

67. The lead as claimed in claim 55, wherein the distal end of the elongated, flexible body member has a tapered shape and a rounded tip.

68. The lead as claimed in claim 55, further comprising a guide catheter that surrounds the intravenous lead during implantation and is adapted to be retracted while leaving the intravenous lead in place.

69. The lead as claimed in claim 68, further comprising dissolvable means for securing the lead to said guide catheter.

70. The lead as claimed in claim 55, wherein said electrode is adapted to be used for defibrillation.

71. The lead as claimed in claim 55, wherein said electrode is adapted to be used for pacing.

72. The lead as claimed in claim 71, further comprising a second electrode coupled to the body member.

73. The lead as claimed in claim 72, wherein said second electrode is adapted to be used for defibrillation.

74. The lead as claimed in claim 72, wherein said second electrode is adapted to be used for bipolar pacing.

75. The lead as claimed in claim 72, further including a separate structure deployable through the lumen past the second opening, the separate structure including the second electrode.

76. The lead as claimed in claim 55, wherein said electrode is adapted to apply a stimulating pulse to the left ventricle.

77. The lead as claimed in claim 55, wherein said body member elutes said steroid.

78. The lead as claimed in claim 55, wherein said coating comprises a steroid eluting collar.

79. For use with a cardiac rhythm management device, a system for implanting an intravenous lead into a coronary vein, comprising:
(1) an intravenous lead, having:
(a) an elongated, flexible body member made of an electrically insulative material and having a coating of an anti-inflammatory agent, said body member having a proximal end and a distal end, said body member being of a size to permit the distal end to be advanced through the right atrium and coronary sinus into the coronary veins;
(b) a lumen extending through the body member from the proximal end toward the distal end of the body member, said lumen having a first opening through the proximal end and a second opening through the distal end of the body member;
(c) a conductive member extending through the body member from the proximal end toward the distal end of the body member; and
(d) an electrode electrically coupled to said conductive member; and
(2) a guide wire for facilitating advancement of the intravenous lead into the coronary veins, said guide wire extending through the first and second openings in said lumen and past the distal end of the body member during implantation of the intravenous lead and being removed from the intravenous lead after placement of the intravenous lead in a selected coronary vein.

80. The system as claimed in claim 79, wherein said coating of an anti-inflammatory agent comprises a carbon coating.

81. The system as claimed in claim 79, wherein said coating of an anti-inflammatory agent comprises a steroid.

82. The system as claimed in claim 81, wherein said coating comprises a steroid eluting collar.

83. The system as claimed in claim 79, further comprising a plug sealing the lumen.

84. The system as claimed in claim 83, wherein said plug is deployable using said lumen.

85. The system as claimed in claim 79, wherein the conductive member comprises a helical coil surrounding the lumen.

86. The system as claimed in claim 85, wherein said lumen has an inner surface comprising a polymer material with a low coefficient of friction.

87. The system as claimed in claim 86, wherein said polymer material is a sleeve contained within the helical coil.

88. The system as claimed in claim 79, wherein said conductive member comprises a tube made of a conductive polymer.

89. The system as claimed in claim 79, wherein said electrode comprises an opening in the body member exposing a portion of the conductive member.

90. The system as claimed in claim 79, wherein said electrode is a ring electrode affixed to the surface of the body member and electrically coupled to said conductive member.

91. The system as claimed in claim 79, wherein said intravenous lead further comprises a second electrode coupled to the body member.

92. The system as claimed in claim 79, wherein said intravenous lead further comprises a separate structure deployable past the distal end and through the lumen, said separate structure including an electrode.

93. The system as claimed in claim 79, wherein the distal end of the elongated, flexible body member has a tapered shape and a rounded tip.

94. The system as claimed in claim 79, further comprising a guide catheter that surrounds the intravenous lead during implantation and is adapted to be retracted while leaving the intravenous lead in place.

95. The system as claimed in claim 94, further comprising dissolvable means for securing the lead to said guide catheter.

96. The system as claimed in claim 79, wherein said electrode is adapted to be used for defibrillation.

97. The system as claimed in claim 79, wherein said electrode is adapted to be used for pacing.

98. The system as claimed in claim 97, further comprising a second electrode coupled to the body member.

99. The system as claimed in claim 98, wherein said second electrode is adapted to be used for defibrillation.

100. The system as claimed in claim 98, wherein said second electrode is adapted to be used for bipolar pacing.

101. The system as claimed in claim 98, further including a separate structure deployable through the lumen past the second opening, the separate structure including the second electrode.

102. The system as claimed in claim 79, wherein said electrode is adapted to apply a stimulating pulse to the left ventrical.

103. For use with a cardiac rhythm management device including a pacemaker for applying pacing pulses to the heart, an intravenous lead having:
  (a) an elongated, flexible body member made of an electrically insulative material and having a coating of an anti-inflammatory agent, said coating comprising a steroid, said body member having a proximal end and a distal end, said body member being of a size to permit the distal end to be advanced through the right atrium and coronary sinus into the coronary veins;
  (b) a lumen extending through the body member from the proximal end toward the distal end of the body member, said lumen having a first opening through the proximal end and a second opening through the distal end of the body member;
  (c) a conducting member extending through the body member from the proximal end toward the distal end of the body member; and
  (d) an electrode electrically coupled to said conductive member and configured to apply pacing pulses to the left ventricle.

104. The lead as claimed in claim 103, wherein said body member elutes said steroid.

105. The lead as claimed in claim 104, wherein said coating comprises a steroid eluting collar, the collar being coupled to said body member.

106. The lead as claimed in claim 103, further including a polymer having a low coefficient of friction which defines said lumen.

107. The lead as claimed in claim 103, wherein said electrode is disposed at a distal end portion of said lead.

108. The lead as claimed in claim 103, wherein said lead has an outer diameter ranging between 0.02 and 0.1 inches.

109. For use with a cardiac rhythm management device including a pacemaker for applying pacing pulses to the heart, an intravenous lead having:
  (a) an elongated, flexible body member made of an electrically insulative material and having a coating of an anti-inflammatory agent, said coating comprising a steroid, said body member having a proximal end and a distal end, said body member being of a size to permit the distal end to be advanced through the right atrium and coronary sinus into the coronary veins;
  (b) a lumen extending through the body member from the proximal end toward the distal end of the body member, said lumen having a first opening through the proximal end and a second opening through the distal end of the body member;
  (c) a conducting member extending through the body member from the proximal end toward the distal end of the body member; and
  (d) a plurality of electrodes, each electrode electrically coupled to said conductive member, at least a first one of the electrodes being configured to apply pacing pulses to the left ventricle.

110. The lead as claimed in claim 109, wherein said electrodes are adapted to be used for bipolar pacing.

111. The lead as claimed in claim 110, wherein at least one of said electrodes is adapted to be used for defibrillation.

112. The lead as claimed in claim 109, further including a separate structure deployable through said lumen, the separate structure including at least one of said electrodes.

113. The lead as claimed in claim 109, wherein said body member elutes said steroid.

114. The lead as claimed in claim 113, wherein said coating comprises a steroid eluting collar, the collar being coupled to said body member.

115. The lead as claimed in claim 109, further including a polymer having a low coefficient of friction which defines said lumen.

116. The lead as claimed in claim 109, wherein at least one of said electrodes is disposed at a distal end portion of said lead.

117. The lead as claimed in claim 109, wherein said lead has an outer diameter ranging between 0.02 and 0.1 inches.

118. For use with a cardiac rhythm management device including a pacemaker for applying pacing pulses to the heart, an intravenous lead system having:
  an intravenous lead having:
    (a) an elongated, flexible body member made of an electrically insulative material and having a coating of an anti-inflammatory agent, said coating comprising a steroid, said body member having a proximal end and a distal end, said body member being of a size to permit the distal end to be advanced through the right atrium and coronary sinus into the coronary veins;
    (b) a lumen extending through the body member from the proximal end toward the distal end of the body member, said lumen having a first opening through the proximal end and a second opening through the distal end of the body member;
    (c) a conducting member extending through the body member from the proximal end toward the distal end of the body member; and
    (d) an electrode electrically coupled to said conductive member, said electrode being configured to apply pacing pulses to the left ventrical; and
  a guide wire for facilitating advancement of the intravenous lead into the coronary veins, said guide wire extending through the first and second openings in said lumen and past the distal end of the body member during implantation of the intravenous lead and being removable from the intravenous lead after placement of the intravenous lead in a selected coronary vein.

119. The system as claimed in claim 118, further comprising a second electrode coupled to the body member.

120. The system as claimed in claim 119, wherein said electrodes are adapted to be used for bipolar pacing.

121. The system as claimed in claim 119, wherein at least one of said electrodes is adapted to be used for defibrillation.

122. The system as claimed in claim 119, further including a separate structure deployable through said lumen, the separate structure including the second electrode.

123. The system as claimed in claim 118, wherein said body member elutes said steroid.

124. The system as claimed in claim 123, wherein said coating comprises a steroid eluting collar, the collar being coupled to said body member.

125. The system as claimed in claim 118, further including a polymer having a low coefficient of friction which defines said lumen.

126. The system as claimed in claim 118, wherein said electrode is disposed at a distal end portion of said lead.

127. The system as claimed in claim 118, wherein said lead has an outer diameter ranging between 0.02 and 0.1 inches.

128. The system as claimed in claim 118, further comprising a guide catheter that surrounds the intravenous lead during implantation and is adapted to be retracted while leaving the intravenous lead in place.

129. For use with a cardiac rhythm management device including a pacemaker for applying pacing pulses to the heart, an intravenous lead having:

(a) an elongated, flexible body member made of an electrically insulative material and having a coating of an anti-inflammatory agent, said coating comprising a steroid, said body member having a proximal end and a distal end, said body member being of a size to permit the distal end to be advanced through the right atrium and coronary sinus into the coronary veins;

(b) a lumen extending through the body member from the proximal end toward the distal end of the body member, said lumen having a first opening through the proximal end and a second opening through the distal end of the body member;

(c) a conducting member extending through the body member from the proximal end toward the distal end of the body member; and (d) an electrode electrically coupled to said conductive member, said electrode being configured to apply a pulse to the left ventricle; and (e) a plug sealing the lumen.

130. The lead as claimed in claim 129, wherein said plug is deployable using said lumen.

131. The lead as claimed in claim 129, further comprising a second electrode coupled to the body member.

132. The lead as claimed in claim 131, wherein said electrodes are adapted to be used for bipolar pacing.

133. The lead as claimed in claim 131, wherein at least one of said electrodes is adapted to be used for defibrillation.

134. The lead as claimed in claim 131, further including a separate structure deployable through said lumen, the separate structure including the second electrode.

135. The lead as claimed in claim 129, wherein said body member elutes said steroid.

136. The lead as claimed in claim 135, wherein said coating comprises a steroid eluting collar, the collar being coupled to said body member.

137. The lead as claimed in claim 129, further including a polymer having a low coefficient of friction which defines said lumen.

138. The lead as claimed in claim 129, wherein said electrode is disposed at a distal end portion of said lead.

139. The lead as claimed in claim 129, wherein said lead has an outer diameter ranging between 0.02 and 0.1 inches.

140. For use with a cardiac rhythm management device including a pacemaker for applying pacing pulses to the heart, an intravenous lead system having:

(a) an elongated, flexible body member made of an electrically insulative material and having a coating of an anti-inflammatory agent, said coating comprising a steroid, said body member having a proximal end and a distal end, said body member being of a size to permit the distal end to be advanced through the right atrium and coronary sinus into the coronary veins;

(b) a lumen extending through the body member from the proximal end toward the distal end of the body member, said lumen having a first opening through the proximal end and a second opening through the distal end of the body member;

(c) a conducting member extending through the body member from the proximal end toward the distal end of the body member; and (d) an electrode electrically coupled to said conductive member, said electrode being configured to apply a pulse to the left ventricle; and (e) a plug sealing the lumen; and (f) a guide wire for facilitating advancement of the intravenous lead into the coronary veins, said guide wire extending through the first and second openings in said lumen and past the distal end of the body member during implantation of the intravenous lead and being removable from the intravenous lead after placement of the intravenous lead in a selected coronary vein.

141. The system as claimed in claim 140, wherein said plug is deployable using said lumen.

142. The system as claimed in claim 140, further comprising a second electrode coupled to the body member.

143. The system as claimed in claim 142, wherein said electrodes are adapted to be used for bipolar pacing.

144. The system as claimed in claim 140, wherein at least one of said electrodes is adapted to be used for defibrillation.

145. The system as claimed in claim 142, further including a separate structure deployable through said lumen, the separate structure including the second electrode.

146. The system as claimed in claim 140, wherein said body member elutes said steroid.

147. The system as claimed in claim 146, wherein said coating comprises a steroid eluting collar, the collar being coupled to said body member.

148. The system as claimed in claim 147, further including a polymer having a low coefficient of friction which defines said lumen.

149. The system as claimed in claim 140, wherein said electrode is disposed at a distal end portion of said lead.

150. The system as claimed in claim 140, wherein said lead has an outer diameter ranging between 0.02 and 0.1 inches.

151. The system as claimed in claim 140, further comprising a guide catheter that surrounds the intravenous lead during implantation and is adapted to be retracted while leaving the intravenous lead in place.

152. A cardiac rhythm management device including a pacemaker for applying pacing pulses to the heart, the device comprising an implantable pulse generator for connection to at least one intravenous lead for use with the cardiac rhythm management device, wherein the improvement comprises a system having:

an intravenous lead having:
(a) an elongated, flexible body member made of an electrically insulative material, said body member having a proximal end and a distal end, said body member being of a size to permit the distal end to be advanced through the right atrium and coronary sinus into the coronary veins;

(b) a lumen extending through the body member from the proximal end toward the distal end of the body member, said lumen having a first opening through the proximal end and a second opening through the distal end of the body member so that a contrasting fluid can be injected through said lumen and out of the distal end of the body member through said second opening;

(c) a conductive member coupled to the pulse generator and extending through the body member from the proximal end toward the distal end of the body member; and (d) an electrode electrically coupled to said conductive member and adapted to apply pacing pulses to the left ventricle; and a guide wire for facilitating advancement of the intravenous lead into the coronary veins, said guide wire extending through the first and second openings in said lumen and past the distal end of the body member during implantation of the intravenous lead and being removable from the intravenous lead after placement of the intravenous lead in a selected coronary vein.

153. The system as claimed in claim 152, further comprising a second electrode coupled to the body member.

154. The system as claimed in claim 153, wherein said electrodes are adapted to be used for bipolar pacing.

155. The system as claimed in claim 153, wherein at least one of said electrodes is adapted to be used for defibrillation.

156. The system as claimed in claim 153, further including a separate structure deployable through said lumen, the separate structure including the second electrode.

157. The system as claimed in claim 152, wherein said body member further comprises a coating of an anti-inflammatory agent.

158. The system as claimed in claim 157, wherein said coating of an anti-inflammatory agent comprises a steroid.

159. The system as claimed in claim 158, wherein said coating comprises a steroid eluting collar, the collar being coupled to said body member.

160. The system as claimed in claim 152, further including a polymer having a low coefficient of friction which defines said lumen.

161. The system as claimed in claim 152, wherein said electrode is disposed at a distal end portion of said lead.

162. The system as claimed in claim 152, wherein said lead has an outer diameter ranging between 0.02 and 0.1 inches.

163. The system as claimed in claim 152, further comprising a guide catheter that surrounds the intravenous lead during implantation and is adapted to be retracted while leaving the intravenous lead in place.

164. A cardiac rhythm management device including a pacemaker for applying pacing pulses to the heart, the device comprising an implantable pulse generator connected to at least one intravenous lead for use with the cardiac rhythm management device, wherein the improvement comprises an intravenous lead having:
   (a) an elongated, flexible body member made of an electrically insulative material, said body member having a proximal end and a distal end, said body member being of a size to permit the distal end to be advanced through the right atrium and coronary sinus into the coronary veins;
   (b) a lumen extending through the body member from the proximal end toward the distal end of the body member, said lumen having a first opening through the proximal end and a second opening through the distal end of the body member so that a contrasting fluid can be injected through said lumen and out of the distal end of the body member through said second opening;
   (c) a conductive member coupled to the pulse generator and extending through the body member from the proximal and toward the distal end of the body member; and
   (d) an electrode electrically coupled to said conductive member and adapted to apply a pacing pulse to the left ventricle; and
   (e) a plug sealing the lumen.

165. The device as claimed in claim 164, wherein said plug is deployable using said lumen.

166. The device as claimed in claim 164, further comprising a second electrode coupled to the body member.

167. The device as claimed in claim 166, wherein said electrodes are adapted to be used for bipolar pacing.

168. The device as claimed in claim 166, wherein at least one of said electrodes is adapted to be used for defibrillation.

169. The device as claimed in claim 166, further including a separate structure deployable throught said lumen, the separate structure including the second electrode.

170. The device as claimed in claim 164, wherein said body member further comprises a coating of an anti-inflammatory agent.

171. The device as claimed in claim 170, wherein said coating of an anti-inflammatory agent comprises a steroid.

172. The device as claimed in claim 171, wherein said coating comprises a steroid eluting collar, the collar being coupled to said body member.

173. The device as claimed in claim 164, further including a polymer having a low coefficient of friction which defines said lumen.

174. The device as claimed in claim 164, wherein said electrode is disposed at a distal end portion of said lead.

175. The device as claimed in claim 164, wherein said lead has an outer diameter ranging between 0.02 and 0.1 inches.

176. A cardiac rhythm management device including a pacemaker for applying pacing pulses to the heart, the device comprising an implantable pulse generator for connection to at least one intravenous lead for use with the cardiac rhythm management device, wherein the improvement comprises a system having:
   an intravenous lead having:
      (a) an elongated, flexible body member made of an electrically insulative material, said body member having a proximal end and a distal end, said body member being of a size to permit the distal end to be advanced through the right atrium and coronary sinus into the coronary veins;
      (b) a lumen extending through the body member from the proximal end toward the distal end of the body member, said lumen having a first opening through the proximal end and a second opening through the distal end of the body member so that a contrasting fluid can be injected through said lumen and out of the distal end of the body member through said second opening;
      (c) a conductive member coupled to the pulse generator and extending through the body member from the proximal end toward the distal end of the body member; and
      (d) an electrode electrically coupled to said conductive member and adapted to apply a pulse to the left ventricle; and
      (e) a plug sealing the lumen; and
   a guide wire for facilitating advancement of the intravenous lead into the coronary veins, said guide wire extending through the first and second openings in said lumen and past the distal end of the body member during implantation of the intravenous lead and being removable from the intravenous lead after placement of the intravenous lead in a selected coronary vein.

177. The system as claimed in claim 176, wherein said plug is deployable using said lumen.

178. The system as claimed in claim 176, further comprising a second electrode coupled to the body member.

179. The system as claimed in claim 178, wherein said electrodes are adapted to be used for bipolar pacing.

180. The system as claimed in claim 178, wherein at least one of said electrodes is adapted to be used for defibrillation.

181. The system as claimed in claim 178, further including a separate structure deployable through said lumen, the separate structure including the second electrode.

182. The system as claimed in claim 176, wherein said body member further comprises a coating of an anti-inflammatory agent.

183. The system as claimed in claim 182, wherein said coating of an anti-inflammatory agent comprises a steroid.

184. The system as claimed in claim 183, wherein said coating comprises a steroid eluting collar, the collar being coupled to said body member.

185. The system as claimed in claim 176, further including a polymer having a low coefficient of friction which defines said lumen.

186. The system as claimed in claim 176, wherein said electrode is disposed at a distal end portion of said lead.

187. The system as claimed in claim 176, wherein said lead has an outer diameter ranging between 0.02 and 0.1 inches.

188. The system as claimed in claim 176, further comprising a guide catheter that surrounds the intravenous lead during implantation and is adapted to be retracted while leaving the intravenous lead in place.

189. A cardiac rhythm management device including a pacemaker for applying pacing pulses to the heart, the device comprising an implantable pulse generator connected to at least one intravenous lead for use with the cardiac rhythm management device, wherein the improvement comprises an intravenous lead having:

(a) an elongated, flexible body member made of an electrically insulative material, said body member having a proximal end and a distal end, said body member being of a size to permit the distal end to be advanced through the right atrium and coronary sinus into the coronary veins;

(b) a lumen extending through the body member from the proximal end toward the distal end of the body member, said lumen having a first opening through the proximal end and a second opening through the distal end of the body member so that a contrasting fluid can be injected through said lumen and out of the distal end of the body member through said second opening;

(c) a conductive member coupled to the pulse generator and extending through the body member from the proximal end toward the distal end of the body member; and (d) a plurality of electrodes, each electrode electrically coupled to said conductive member, at least one said electrodes being adapted to apply a pacing pulse to the left ventricle.

190. The device as claim in claim 189, wherein said electrodes are adapted to be used for bipolar pacing.

191. The device as claim in claim 190, wherein at least one of said electrodes is adapted to deliver a defibrillation pulse.

192. The device as claimed in claim 189, further including a polymer having a low coefficient of friction which defines said lumen.

193. The device as claimed in claim 189, wherein at least one of said electrodes is disposed at a distal end portion of said lead.

194. For use with a cardiac rhythm management device, a system for implanting an intravenous lead into a coronary vein, comprising:

(1) an intravenous lead, having:

(a) an enlongated, flexible body member made of an electrically insulative material and having a coating of an anti-inflammatory agent, said body member having a proximal end and a distal end, said body member being of a size to permit the distal end to be advanced through the right atrium and coronary sinus into the coronary veins;

(b) a lumen extending through the body member from the proximal end toward the distal end of the body member, said lumen having a first opening through the proximal end and a second opening through the distal end of the body member;

(c) a conductive member comprising a helical coil formed around said lumen, said conducting member extending through the body member from the proximal end toward the distal end of the body member; and (d) an electrode electrically coupled to said conductive member, for providing a stimulating pulse to the left ventricle upon insertion of the lead into a coronary vein;

(2) a guide wire for facilitating advancement of the intravenous lead into the coronary veins, said guide wire extending through the first and second openings in said lumen and past the distal end of the body member during implantation of the intravenous lead and being removed from the intravenous lead after placement of the intravenous lead in a selected coronary vein; and (3) a plug sealing the lumen.

195. For use with a permanently implantable cardiac rhythm management device for applying pacing pulses to the left ventricle of the heart, a permanently implantable intravenous lead having:

(a) an elongated, flexible body member made of an electrically insulative material, said body member having a proximal end and a distal end, said body member being of a size to permit the distal end to be advanced through the right atrium and coronary sinus into the coronary veins and permanently implanted in the body;

(b) a lumen extending through the body member from the proximal end toward the distal end of the body member, said lumen having a first opening through the proximal end and a second opening through the distal end of the body member so that a contrasting fluid can be injected through said lumen and out of the distal end of the body member through said second opening;

(c) a conductive member extending through the body member from the proximal end toward the distal end of the body member;

(d) an electrode electrically coupled to said conductive member and adapted to applying pacing pulses to the left ventricle; and (e) a collar coupled to the body member, the collar including an anti-inflammatory agent.

196. The lead as claimed in claim 195, wherein the collar is a steroid eluting collar.

197. The lead as claimed in claim 196, further comprising a plug sealing the lumen.

198. The lead as claimed in claim 196, wherein the conductive member comprises a helical coil surrounding the lumen.

199. The lead as claimed in claim 198, wherein said lumen has an inner surface comprising a polymer material with a low coefficient of friction.

200. The lead as claimed in claim 199, wherein said polymer material is a sleeve contained within the helical coil.

201. The lead as claimed in claim 196, wherein said conductive member comprises a tube made of a conductive polymer.

202. The lead as claimed in claim 196, wherein said electrode comprises an opening in the body member exposing a portion of the conductive member.

203. The lead as claimed in claim 196, wherein said electrode is a ring electrode affixed to the surface of the body member and electrically coupled to said conductive member.

204. The lead as claimed in claim 196, wherein said intravenous lead further comprises a second electrode coupled to the body member.

205. The lead as claimed in claim 196, wherein the distal end of the elongated, flexible body member has a tapered shape and a rounded tip.

206. The lead as claimed in claim 196, further comprising a guide catheter that surrounds the intravenous lead during implantation and is adapted to be retracted while leaving the intravenous lead implanted in a coronary vein.

207. The lead as claimed in claim 196, wherein said electrode is adapted to be used for defibrillation.

208. The lead as claimed in claim 196, wherein said electrode is adapted to be used for pacing.

209. The lead as claimed in claim 208, further comprising a second electrode coupled to the body member.

210. The lead as claimed in claim 209, wherein said second electrode is adapted to be used for defibrillation.

211. The lead as claimed in claim 209, wherein said second electrode is adapted to be used for bipolar pacing.

212. The lead as claimed in claim 196, wherein said electrode is adapted to apply a stimulating pulse to the left ventricle.

213. For use with a permanently implantable cardiac rhythm management device including a pacemaker for applying pacing pulses to the heart, a intravenous lead system having:
   a permanently implantable intravenous lead having:
   (a) an elongated, flexible body member made of an electrically insulative material, said body member having a proximal end and a distal end, said body member being of a size to permit the distal end to be advanced through the right atrium and coronary sinus into the coronary veins and permanently implanted in the body;
   (b) a lumen extending through the body member from the proximal end toward the distal end of the body member, said lumen having a first opening through the proximal end and a second opening through the distal end of the body member so that a contrasting fluid can be injected through said lumen and out of the distal end of the body member through said second opening;
   (c) a conductive member extending through the body member from the proximal end toward the distal end of the body member;
   (d) an electrode electrically coupled to said conductive member and adapted to apply pacing pulses to the left ventricle; and
   (e) a collar coupled to the body member, the collar including an anti-inflammatory agent; and
   a guide wire for facilitating advancement of the intravenous lead into the coronary veins, said guide wire extending through the first and second openings in said lumen and past the distal end of the body member during implantation of the intravenous lead and being removable from the intravenous lead after placement of the intravenous lead in a selected coronary vein.

214. The system as claimed in claim 213, wherein the collar is a steroid eluting collar.

215. The system as claimed in claim 214, further comprising a second electrode coupled to the body member.

216. The system as claimed in claim 215, wherein said electrodes are adapted to be used for bipolar pacing.

217. The system as claimed in claim 215, wherein at least one of said electrodes is adapted to be used for defibrillation.

218. The system as claimed in claim 214, further including a polymer having a low coefficient of friction which defines said lumen.

219. The system as claimed in claim 214, wherein said electrode is disposed at a distal end portion of said lead.

220. The system as claimed in claim 214, wherein said lead has an outer diameter ranging between 0.02 and 0.1 inches.

221. The system as claimed in claim 214, further comprising a guide catheter that surrounds the intravenous lead during implantation and is adapted to be retracted while leaving the intravenous lead implanted in a coronary vein.

222. A cardiac rhythm management system including a pacemaker for applying pacing pulses to the heart, the system comprising an implantable pulse generator for connection to at least one intravenous lead for use with the cardiac rhythm management system, wherein the improvement comprises a system having:
   an intravenous lead having:
   (a) an elongated, flexible body member made of an electrically insulative material, said body member having a proximal end and a distal end, said body member comprising an outer diameter ranging between 0.02 and 0.1 inches and being of a size to permit the distal end to be advanced through the right atrium and coronary sinus into the coronary veins, said proximal end including a connector for mating with the pacemaker;
   (b) a lumen extending through the body member from the proximal end toward the distal end of the body member, said lumen having a first opening through the proximal end and a second opening through the distal end of the body member so that a contrasting fluid can be injected through said lumen and out of the distal end of the body member through said second opening;
   (c) a conductive member coupled to the pulse generator and extending through the body member from the proximal end toward the distal end of the body member;
   (d) an electrode electrically coupled to said conductive member, the electrode being configured to apply a pacing pulse to the left ventricle; and
   (e) a steroid eluting collar coupled to the body member; and
   a guide wire for facilitating advancement of the intravenous lead into the coronary veins, said guide wire extending through the first and second openings in said lumen and past the distal end of the body member during implantation of the intravenous lead and being removable from the intravenous lead after placement of the intravenous lead in a selected coronary vein.

223. The device as claimed in claim 222, wherein the conductive member comprises a helical coil surrounding the lumen.

224. The device as claimed in claim 223, further comprising a guide catheter that surrounds the intravenous lead during implantation and is adapted to be retracted while leaving the intravenous lead in place.

225. The device as claimed in claim 224, further comprising a plug sealing the lumen.

226. The device as claimed in claim 222, 223, 224, or 225, wherein said electrode is located at the distal end portion of the lead.

227. The device as claimed in claim 222, 223, 224 or 225, further including a second electrode coupled to the body member, said lead configured to bipolar pace using siad electrodes.

228. For use with a permanently implantable cardiac rhythm management device for applying pacing therapy to the heart, a permanently implantable intravenous lead having:

(a) an elongated, flexible body member made of an electrically insulative material, said body member having a proximal end and a distal end, said body member comprising an outer diameter ranging between 0.02 and 0.1 inches and being of a size to permit the distal end to be advanced through the right atrium and coronary sinus into the coronary veins and permanently implanted in the body, said proximal end including a connector for mating with the pacemaker;

(b) a lumen extending through the body member from the proximal end toward the distal end of the body member, said lumen having a first opening through the proximal end and a second opening through the distal end of the body member so that a contrasting fluid can be injected through said lumen and out of the distal end of the body member through said second opening;

(c) a conductive member extending through the body member from the proximal end toward the distal end of the body member;

(d) an electrode electrically coupled to said conductive member, the electrode being configured to apply pacing pulses to the left ventricle; and (e) a steroid eluting collar coupled to the body member.

229. The lead as claimed in claim 228, wherein the conductive member comprises a helical coil surrounding the lumen.

230. The lead as claimed in claim 229, further comprising a guide catheter that surrounds the intravenous lead during implantation and is adapted to be retracted while leaving the intravenous lead implanted in a coronary vein.

231. The lead as claimed in claim 230, further comprising a plug sealing the lumen.

232. A lead as claimed in claims 228, 229, 230, or 231, further including a second electrode coupled to the body member, said electrodes adapted for bipolar pacing.

233. A lead as claimed in claims 228, 229, 230, or 231, wherein said electrode is located at the distal end portion of the lead.

234. The device according to claims 7, 10, 55, 79, 103, 118, 129, 140, 152, 164, 176, 194, 195, 213, 222, 223, 224, 225, 228, 229, 230, or 231, wherein said lead consists only of one electrode.

235. The device according to claims 1, 10, 152, 164, 176, or 189, wherein the body member further comprises an anti-inflammatory agent.

* * * * *